(12) United States Patent
Mitra et al.

(10) Patent No.: US 7,767,233 B2
(45) Date of Patent: Aug. 3, 2010

(54) NATURAL HAIR CARE COMPOSITION, METHODS FOR OBTAINING THE SAME AND USE THEREOF

(75) Inventors: Shanker Kumar Mitra, Karnataka (IN); Ekta Saxena, Karnataka (IN); Uddagiri Venkanna Babu, Karnataka (IN); Marikunte Venkata Ranganna, Karnataka (IN)

(73) Assignee: Himalaya Global Holdings, Ltd., Dubai (AE)

( * ) Notice: Subject to any disclaimer, the term of this patent is extended or adjusted under 35 U.S.C. 154(b) by 1319 days.

(21) Appl. No.: 10/995,369

(22) Filed: Nov. 24, 2004

(65) Prior Publication Data

US 2006/0029557 A1 Feb. 9, 2006

(30) Foreign Application Priority Data

Aug. 6, 2004 (IN) .................. 1462/DEL/2004

(51) Int. Cl.
*A61K 36/00* (2006.01)
(52) U.S. Cl. .................................... 424/725
(58) Field of Classification Search ............... None
See application file for complete search history.

(56) References Cited

U.S. PATENT DOCUMENTS

| | | | |
|---|---|---|---|
| 4,933,177 A * | 6/1990 | Grollier et al. | 424/74 |
| 5,000,949 A | 3/1991 | Bias | |
| 5,135,746 A * | 8/1992 | Matsuno et al. | 424/725 |
| 5,858,371 A * | 1/1999 | Singh et al. | 424/731 |
| 6,203,782 B1 | 3/2001 | Eliaz et al. | |
| 6,358,541 B1 | 3/2002 | Goodman | |
| 6,365,199 B1 | 4/2002 | Olguin | |
| 6,416,773 B2 * | 7/2002 | Heidenfelder et al. | 424/401 |
| 6,447,762 B1 | 9/2002 | Casadó | |
| 6,451,777 B1 | 9/2002 | Bradbury et al. | |
| 6,495,174 B1 | 12/2002 | Niazi | |
| 2003/0031722 A1 * | 2/2003 | Cao et al. | 424/493 |

OTHER PUBLICATIONS

Bhatnager et al, Biological Activity of Indian Medical Plants, J. Med. Res., 1961, 799-813.
Phadke, Sense Organs, Associated Structures and Functions, Biological Abstracts, 1983, p. 76, ref No. 90478.
Datsur, Medical Plants of India and Pakistan, Useful Plants of India and Pakistan Handbook, 1952, pp. 42-43.
S. R. Gupta, et al. The Glucosides of Bueta Monosperma, Phytochemistry, 1970, pp. 2231-2235.
Gupta, Forest Flora of the Chakrata, Dehra Dun and Saharanpur Forest Divisions United Provinces, Calcutta Government of India Central Publication Branch, 1928, pp. 178-181.
Indian Pharmaceutical Codex, General Monographs, pp. 133-134, 1953.
Khanna and Chaudhry, Antifertility Screening of Plants, Department of Pharmacology, Post graduate Institute of Medical Eduction and Research, Chandigarh, India, 1968, pp. 1575-1580.
Oke et al., Chalcones Form Butea Frondosa L. Flower Extract As Yellow Food Colorants, Journal of Food Science, vol. 45, 1980, pp. 746-747.
Takahashi et al, The First Clinical Trial of Topical Application of Procyanidin B-2 to Investigate Its Potential As a Hair Growing Agent, Phytotheray Research, vol. 15, 2001, 331-336.
Prakash et al., Screening of Indian Plants for Antifertility Activity, Indian J. Exp. Biol., 1967, pp. 623-626.
Puri et al., Survey of Anthoxanthins, Journal of Chemical Society, pp. 1589-1595, 1955.
Shah et al., Phytochemical Studies and Antioestrogenic Activity of Butea Frondosa Flowers, Indian J. Pharma Sci., 1990, pp. 272-275.
Singh et al, Some Vegetable Tannin Materials of Jammu and Kashmir, Indian For., 1958, pp. 571-576.
Srivastava et al., Medical Potentials of Some Indian LAC Host Plants, The Eastern Pharmacist, 1982, pp. 47-50.
Vohora, Research on Medicinal Plants in India, Indian Drugs, vol. 26, 1989, pp. 526-532.

* cited by examiner

*Primary Examiner*—Christopher R Tate
*Assistant Examiner*—Melenie McCormick
(74) *Attorney, Agent, or Firm*—Pillsbury Winthrop Shaw Pittman LLP

(57) ABSTRACT

Disclosed is a natural hair care composition comprising extract of flowers of plant *Butea frondosa* and/or stem bark of plant *Butea parviflora*, and/or the exudates of stem and root of plant *Butea superba*, and a cosmetically acceptable carrier. Also disclosed are methods for obtaining the plant extract and use thereof in regulation of hair growth and prevention of hair loss in all kinds of hair disorders.

13 Claims, 6 Drawing Sheets

NATURAL HAIR CARE COMPOSITION, METHODS FOR OBTAINING THE SAME AND USE THEREOF

FIELD OF THE INVENTION

This invention in general relates to the field of cosmetology. More particularly the present invention provides a natural cosmetic composition comprising extract of *Butea frondosa* and/or *Butea parviflora* and/or *Butea superba* and cosmetically acceptable carrier. This composition is safe and effective for controlling hair loss in human beings.

BACKGROUND OF THE INVENTION

Hair loss is primarily a cosmetic problem in humans. It occurs in different kinds of situations and includes male pattern alopecia, alopecia sinilis, alopecia greata, diseases accompanied by skin lesions or tumors and systemic disorders such as nutritional disorder. Chemotherapy induced alopecia is another kind of hair loss situation in cancer chemotherapy for which no effective therapy is readily available.

Hair care sector has a big market potential. It is estimated that hair care products have a market of $ 6 billion in U.S. alone. In India the estimated market for hair care products is around Rs. 26 billion.

There are many products in the market, which claim enhancement of hair growth and prevention of hair loss but are expensive and associated with side effects. For example, Minoxidil a conventional drug provides moderate regrowth of hair on bald areas of the scalp. The medication is to be applied to balding spots twice a day and must be continued daily. Recurrence of Hair loss is usual if application is stopped. Oral Minoxidil is reported to affect heart rate in some patients, so people having cardiovascular problems can use topical form only.

In recent times, many herbal drugs have been developed which are claimed to be safe and effective to treat hair loss and regulate hair growth in cases of chemotherapy induced alopecia. In Chinese medicine, traditional tonics comprising herbs such as *Polygonum multiflorum*, Lycium fruits, Chinese Foxglove root, Dioscorea opposita and Cornus officinalis are reported for hair growth and prevention of hair loss.

To overcome the side effects of synthetic hair care products and also lack of systematic scientific evaluation of herbal products, many research findings are aimed at scientific evaluation of herbal products for its better therapeutic efficacy and mechanism of action. The present invention is therefore an outcome of a systematic evaluation of herbal materials based on their active compounds and development of a natural composition for prevention of hair loss and regulation of hair growth, which is safe and affordable.

RELATED ART

U.S. Pat. No. 6,495,174 to Niazi, discloses a composition comprising alcoholic extracts of herbs Rhizoma Zinziberis Recens, Rhizoma pinelliae, Flos carthami, Radix rehmanniae, Radix angelicae sinensis, Radix paenoiae rubra, Cacumen biotae, Semen sesami nigruin, Radix polydoni multiflori, Fructus mori combined with Tincture Capsicum, Tincture Cantharidinate and Oleum Ricini for direct application to scalp for the treatment of all kinds of alopecia in humans.

U.S. Pat. No. 6,447,762 to Casado, describes the preparation of a hair lotion for hair protecting action and prevention of hair loss comprising extracts of herbs *Humulus lupulus*, *Rosmarinus officinalis* and *Swertia japonica* and *Silanodiol salicylate* and other pharmaceutically acceptable carriers.

U.S. Pat. No. 6,365,199 to Olguin, reports a hair growth formulation comprising of lemon peel extract including bioflavonoids membrane and castor oil.

U.S. Pat. No. 6,451,777 to Bradbury, et. al., teaches a composition containing a compound from the group consisting of lupane triterpenes, derivatives of lupane, oleanane, ursane triterpenes and salts thereof for regulating hair growth and loss of hair.

U.S. Pat. No. 6,358,541 to Goodman, disclosed improved compositions comprising saw palmetto berry extract containing phytosterols and one or more low irritability constituents that enhance penetration of the extract into hair follicular pores, for the treatment of androgenetic alopecia.

U.S. Pat. No. 6,203,782 to Eliaz, et. al., discloses methods and compositions for promoting hair growth, preventing or minimizing hair loss, enhancing or restoring hair color or remelanization and treating other hair and skin conditions. The compositions include as an essential component a treatment agent in an amount effective for treating the condition, preferably selected from the class of herbs consisting of *Foeniculum vulgares* (fennel seed), *Pimpinella anisum* (anise), *Carum carvi* (caraway seeds) and mixtures thereof with each other and/or other herbs.

U.S. Pat. No. 5,000,949 to Bias, discloses a hair grooming composition, which promotes scalp and hair health and growth, comprising petroleum jelly, an oil extract of cactus, glycerin and oil of clover or other odorant and method of producing the composition.

T. Takahashi et. al., reported that Procynidin B-2 isolated from Apple juice acts as growth promoting factor on murine hair epithelial cells. Procyanidin B-2 therapy showed potential as promising cure for male pattern baldness (Phytother. Res. 15, 331-36, 2001).

SUMMARY OF THE INVENTION

It is the principal aspect of the present invention to disclose the effect of the extracts of plant *Butea frondosa*, *Butea superba* and plant *Butea parviflora* to regulate hair growth and prevention of hair fall due to all kinds of alopecia.

In another aspect, the present invention discloses the efficacy of the extracts of plants *Butea frondosa*, *Butea superba* and *Butea parviflora* alone or in combination thereof as hair growth promoter.

In still another aspect, the present invention provides for a cosmetic composition containing a therapeutically effective amount of extracts of plants *Butea frondosa*, *Butea superba* and *Butea parviflora* alone or in combination thereof.

In yet another aspect, the present invention provides for a cosmetic composition containing a therapeutically effective amount of extracts of plants *Butea frondosa*, *Butea superba* and *Butea parviflora* or a natural hair care composition comprising said extract of said plants, in a cosmetically acceptable carrier or otherwise.

In one another aspect, the present invention provides for determining the role of a therapeutically effective amount of extracts of plants *Butea frondosa*, *Butea superba* and *Butea parviflora* in all kinds of alopecia.

In yet another aspect, the present invention discloses methods of treating patients suffering from diffused hair loss and also to regulate hair growth in alopecia cases.

In another aspect, the present invention discloses methods of producing extracts from plants *Butea frondosa*, *Butea superba* and *Butea parviflora*.

In one preferred embodiment, there is provided a natural hair care composition comprising a therapeutically effective amount of the extracts of plant *Butea frondosa, Butea superba* and *Butea parviflora* wherein the extract of plant *Butea frondosa* is prepared using all parts of said herb *Butea frondosa* and preferably its flowers.

In another preferred embodiment, there is provided a natural hair care composition comprising a therapeutically effective amount of the extract of plant *Butea frondosa, Butea superba* and *Butea parviflora* wherein the extract of plant *Butea superba* is prepared using all parts of said herb *Butea superba* and preferably its exudates from stem and roots.

In still another preferred embodiment, there is provided a natural hair care composition comprising a therapeutically effective amount of the extract of plant *Butea frondosa, Butea superba* and *Butea parviflora* wherein the extract of plant *Butea parviflora* is prepared using all parts of said herb *Butea parviflora* and preferably its stem bark.

In one preferred embodiment, there is provided a natural hair care composition comprising an aqueous-acetone extract of coarse powder of flowers of plant *Butea frondosa*.

In another preferred embodiment, there is provided a natural hair care composition comprising an aqueous-acetone extract of coarse powder of stem bark of plant *Butea parviflora*.

In another preferred embodiment, there is provided a natural hair care composition comprising an aqueous-acetone extract of coarse powder of exudates or resin from stem and root of *Butea superba*.

In another preferred embodiment, there is provided a natural hair care composition comprising an aqueous-acetone extract of a herbal mixture comprising the coarse powders of flowers of *Butea frondosa*, stem bark of *Butea parviflora* and exudates or resin from stem and root of *Butea superba*.

In one preferred embodiment, there is provided a natural hair care composition comprising extraction of flowers of *Butea frondosa* with all organic solvents like hexane, chloroform, dichloromethane, ethyl acetate, acetone, methanol, ethyl alcohol, water and preferably a mixture of acetone and water in the ratio of 7:3.

In yet another preferred embodiment, there is provided a natural hair care composition coinprising a therapeutically effective amount of extract of plant *Butea frondosa* comprising Alkaloids, Amino acids (Cysteine, Aspartic acid), Procyanidins, Tannins, Flavonoids, Saponins, Glycosides, Reducing Sugars, Bitters, Fixed oil and anthraquinones as active constituents.

In yet another preferred embodiment, there is provided a natural hair care composition containing a therapeutically effective amount of extracts of plants *Butea frondosa* and *Butea parviflora* and a cosmetically acceptable carrier wherein the composition is for an external application in the form of cream or gel.

In another preferred embodiment, there is provided a natural hair care composition containing a therapeutically effective amount of extracts of plants *Butea frondosa* or *Butea parviflora* or a combination of the two, in an amount of 1% to 5% and cosmetically acceptable carriers comprising Light liquid paraffin: 3.0%, Isopropyl myristate: 1.0%, Caprylic capric triglyceride: 0.5%, Cetyl alcohol: 1.0%, Cresmer 1000: 0.8%, Glyceryl mono hydroxy stearate: 0.6%, Sorbitan stearate: 0.6%, Polysorbate: 0.6%, BHT: 0.1%, Carbomer: 0.5%, Glycerin: 2.0%, EDTA: 0.05% and Triethanolamine: 0.4% for the preparation of hair cream.

In still another preferred embodiment, there is provided a natural hair care composition containing a therapeutically effective amount of extracts of plants *Butea frondosa, Butea superba* and plant *Butea parviflora* alone or in combination thereof in an amount of 1% to 5% and cosmetically acceptable carriers comprising Light liquid paraffin: 3.0%, Isopropyl myristate: 1.0%, Caprylic capric triglyceride: 0.5%, Cetyl alcohol: 1.0%, Cresmer 1000: 0.8%, Glyceryl mono hydroxy stearate: 0.6%, Sorbitan stearate: 0.6%, Polysorbate: 0.6%, BHT: 0.1%, Carbomer: 0.5%, Glycerin: 2.0%, EDTA: 0.05% and Triethanolamine: 0.4% for the preparation of hair cream.

In another preferred embodiment, there is provided a natural hair care composition containing a therapeutically effective amount of extracts of plants *Butea frondosa* or *Butea parviflora* or a combination of the two in an amount of 1% to 5% and cosmetically acceptable carriers comprising Carbomer: 0.5%, Triethanolamine: 0.2%, Sodium salt of methyl paraben 0.2% and propyl paraben: 0.1% and glycerin: 5% for the preparation of hair gel.

In still another preferred embodiment, there is provided a natural hair care composition containing a therapeutically effective amount of extracts of plants *Butea frondosa, Butea superba* and plant *Butea parviflora* alone or in combination thereof in an amount of 1% to 5% and cosmetically acceptable carriers comprising Carbomer: 0.5%, Triethanolamine: 0.2%, Sodium salt of methyl paraben 0.2% and propyl paraben: 0.1% and glycerin: 5% for the preparation of hair gel.

In yet another preferred embodiment, there is provided a natural hair care composition comprising a potency equivalent of the extract ranging from about 1% to about 5%.

In a still preferred embodiment, there is provided a method of treating hair growth deficiencies by applying sufficient quantity of hair cream or hair gel with slight massage on the scalp, concentrating on the affected area, daily in morning and evening and the treatment should be continued until satisfactory results are obtained.

In still another preferred embodiment, there is provided a natural hair care composition, wherein the composition is used for regulating hair growth and preventing hair fall in all kinds of alopecia.

In still another preferred embodiment, there is provided a process for obtaining a natural hair care composition, wherein the process comprises extracting *Butea frondosa* flowers by percolation, filtering the plant extract, concentrating the plant extract to dryness on rotatory evaporator or on steam bath at optimum temperature and producing natural hair care composition comprising said dry extract and cosmetically acceptable carrier.

In still another preferred embodiment of the present invention, there is provided a process for preparation of a natural hair care composition, wherein the method comprises extracting plant extract from *Butea frondosa* by hot soxhalation, filtering the plant extract, concentrating the plant extract to dryness on rotatory evaporator or on steam bath at optimum temperature and producing a natural hair care composition employing said dry extract and cosmetically acceptable carrier.

In still another preferred embodiment of the present invention, there is provided a process for preparation of a natural hair care composition, wherein the method comprises extracting plant extract from *Butea parviflora* by percolation, filtering the plant extract, concentrating the plant extract to dryness on rotatory evaporator or on steam bath at optimum temperature and producing a natural hair care composition employing said dry extract and cosmetically acceptable carrier.

In still another preferred embodiment of the present invention, there is provided a process for preparation of a natural hair care composition, wherein the method comprises extracting plant extract from *Butea parviflora* by hot soxhalation, filtering the plant extract, concentrating the plant extract to dryness on rotatory evaporator or on steam bath at optimum temperature and producing a herbal composition employing said dry extract and cosmetically acceptable carrier.

BRIEF DESCRIPTION OF DRAWINGS

Further objects of the present invention together with additional features contributing thereto and advantages accruing there from will be apparent from the description of preferred embodiments of the present invention which are shown in the accompanying drawings.

DETAILED DESCRIPTION OF THE INVENTION

Figure 1A:
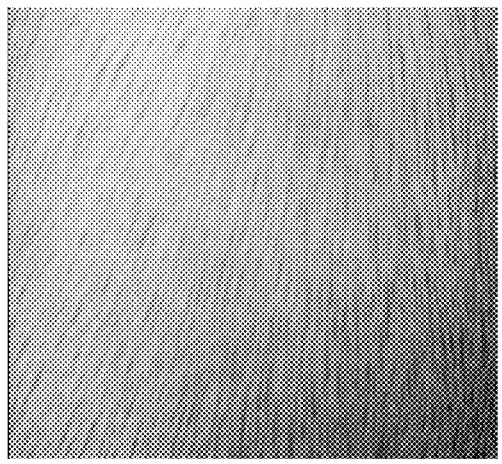
FIGS. 1A & 1B is stereosome Photograph showing normal hair growth in Control animals.
Figure 1B:
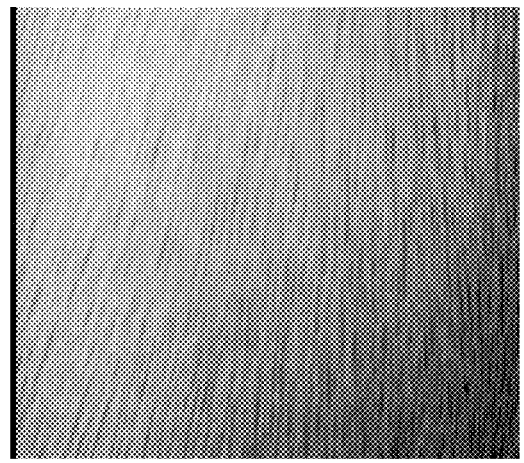
Figure 2A:
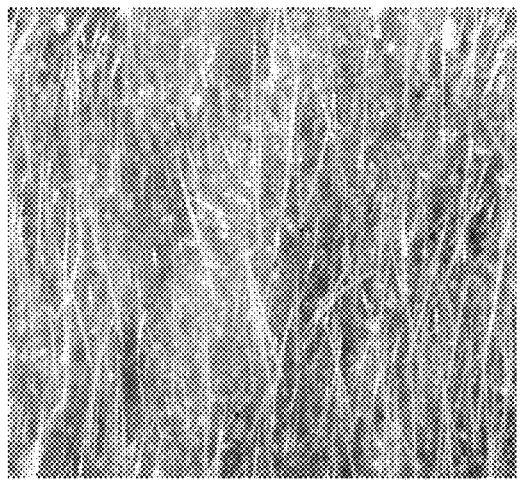
FIGS. 2A & 2B is stereosome Photograph showing scanty hairs in CP treated animals.
Figure 2B:
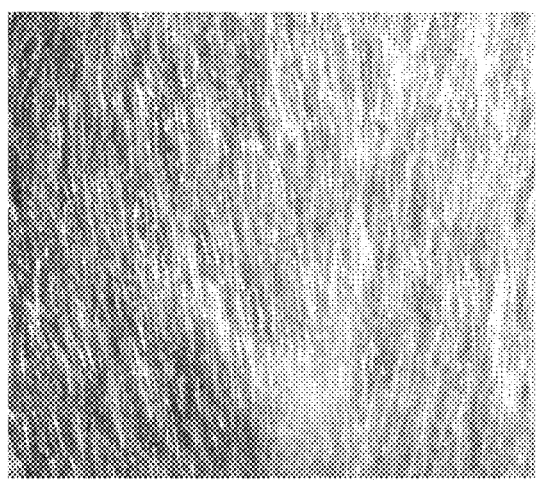
Figure 3A:
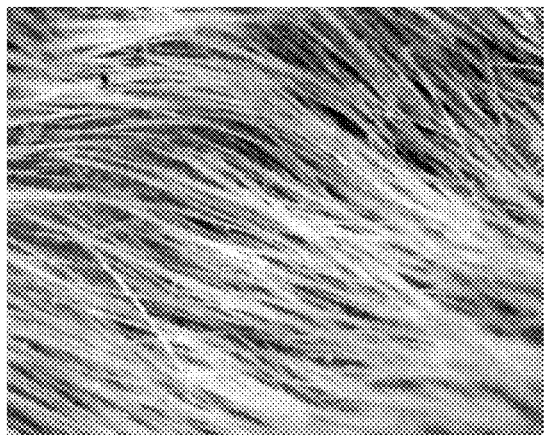
FIGS. 3A, 3B & 3C is stereosome Photograph showing considerable degree of hair growth in PCPB-80 treated animals.
Figure 3B:
Figure 3C:
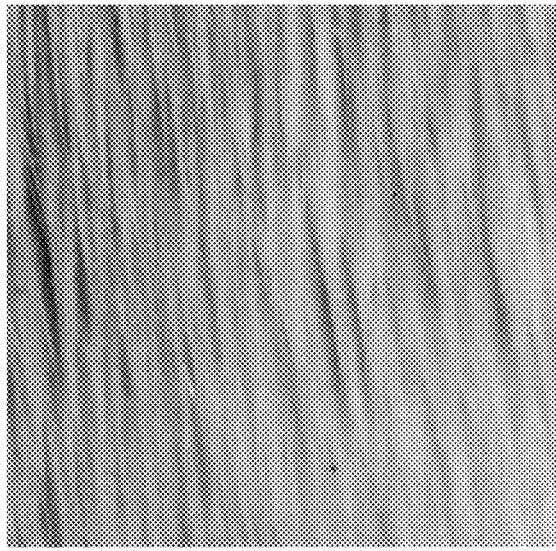
Figure 4:
FIG. 4 is rat pups showing normal hair growth in control group.
Figure 5:
FIG. 5 is rat pups showing high degree of alopecia in CP treated group.
Figure 6:
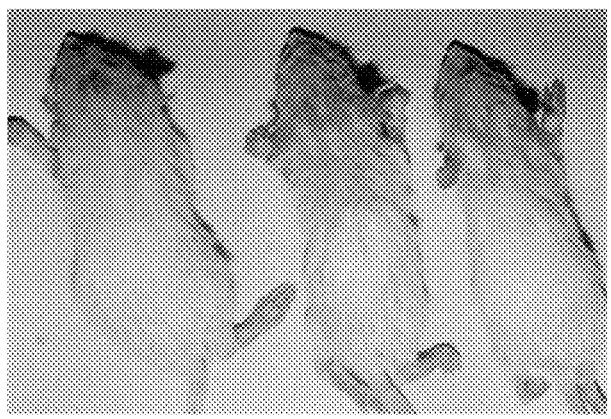
FIG. 6 is rat pups showing protection against CP induced alopecia with PCPB-80.
Figure 7:
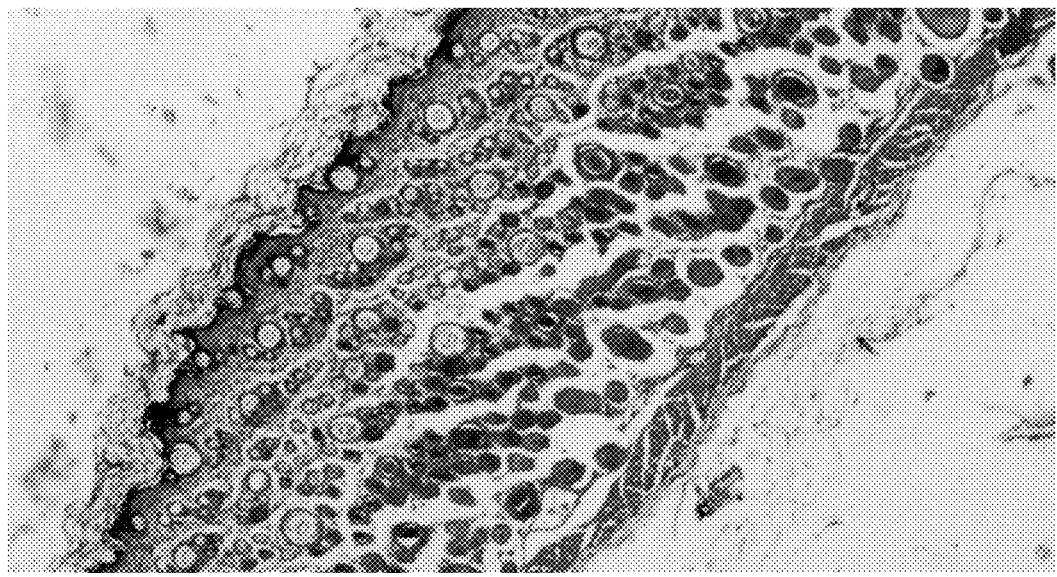
FIG. 7 is photomicrograph of skin section showing normal adenexal components in dermis of normal animals.
Figure 8:
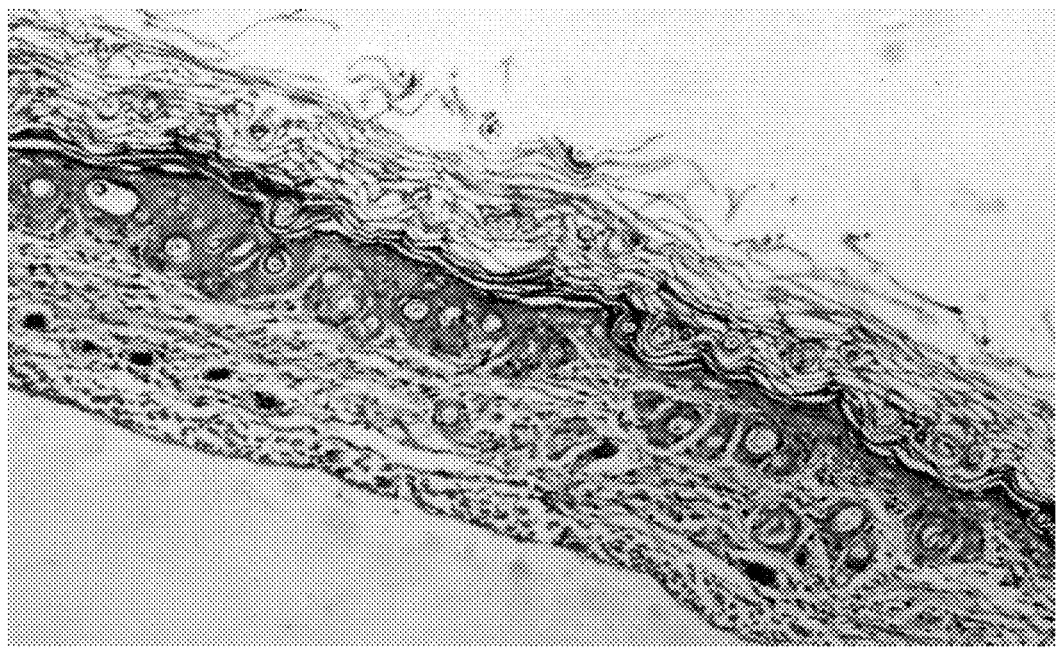
FIG. 8 is photomicrograph of skin section showing degenerating hair follicles with decrease in their numbers in CP treated group.
Figure 9:
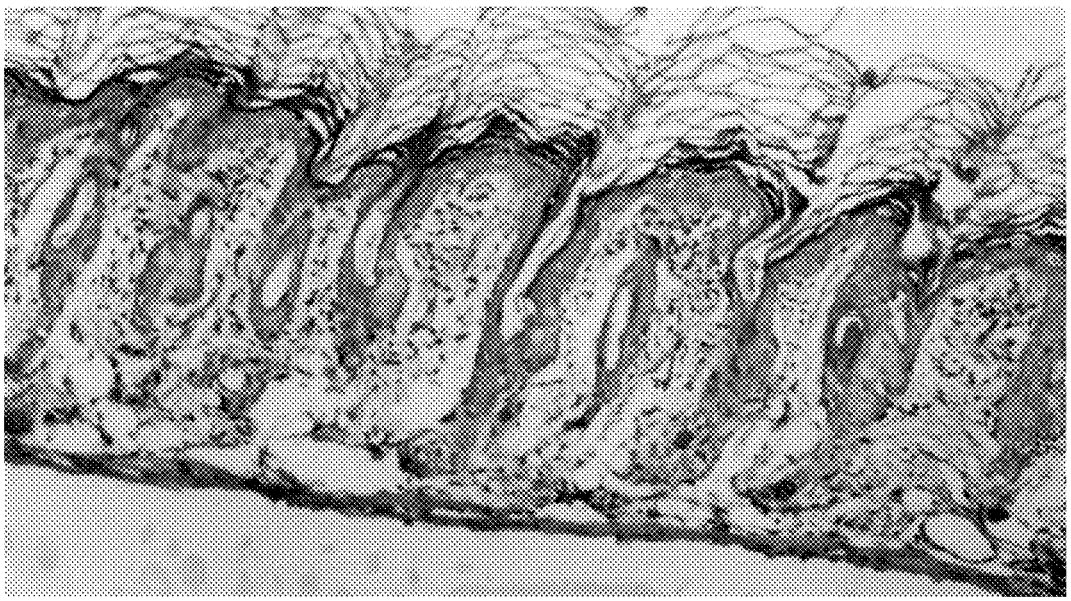
FIG. 9 is photomicrograph of skin section showing degenerating hair follicles with epidermal down growth in CP treated group.
Figure 10A:
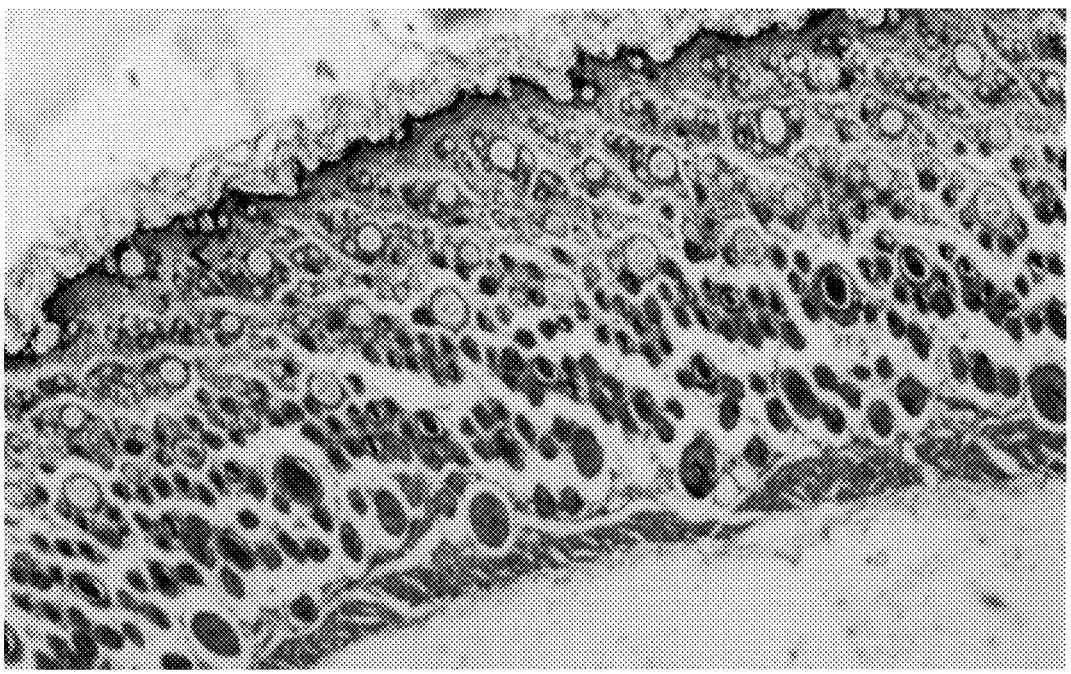
FIGS. 10A & 10B is photomicrograph of skin section showing considerable number of hair follicles with few degenerated follicles in CP+PCPB-80 treated group.
Figure 10B:

The present invention involves the selection and identification of the herbs and obtaining the extract by subjecting the same to solvent extraction. The present invention also involves the bioassay guided fractionation of the extract to identify the active markers or active fraction and to develop effective and safe composition for use in human beings in cases of severe hair fall and regulation of hair growth.

*Butea frondosa* syn monospermal, is a deciduous tree with a somewhat crooked trunk, up to 15 m in height and 1.6-2.0 m (sometimes up to 3.8 m) in girth; commonly found throughout India, except in the arid regions. Bark bluish gray or light brown; leaves long-petioled, 3-foliolate, leaflets coriaceous, broadly obovate from a cuneate or deltoid base, glabrescent above, densely finely silky below; flower buds dark brown, flowers bright orange-red, sometimes yellow, in 15 cm long racemes on bare branches.

The fresh juice from stem bark is applied to ulcers and in relaxed, congested, and septic sore throat. The gum is a powerful astringent; it is given internally for diarrhoea and dysentery, phthisis and haemorrhage from stomach and bladder; its infusion is occasionally employed as a local application in leucorrhoea. A solution of the gum is applied to bruises and erysipelatous inflammations and ringworm. [Wallis, 454; I.P.C., 134; Dastur, Useful Plants, 54; Kirtikar & Basu, 1,187; Billore & Audichya, J Res Indian Med, Yoga, 1978, 13 (2), 104]. The gum contains leucocyanidin, its tetramer, procyanidin, gallic acid and mucilaginous material. It is edible, rich in riboflavin (138.8 µg/g) and also contains thiamine (4.3 µg/g). On dry distillation it gives pyrocatechin.

The bark is reported to possess astringent, bitter, pungent, alterative, aphrodisiac and anthelmintic properties. It is useful in tumours, bleeding piles and ulcers. The decoction is prescribed in cold, cough, fever, various forms of haemorrhages, in menstrual disorders and in the preparation of tonics and elixirs. A fraction containing the sodium salt of phenolic constituents isolated from the bark has shown potential as an anti-asthmatic agent in experimental animals. Analysis of the bark gave: total water-sol extr, 13.80; tannins, 5.82; and non-tannins, 7.98%; and colour (Lovibond). R-6, Y-7.8 (Mooss, 57; Rama Rao, 121; Puri, Quart J Crude Drug Res, 1970, 10, 1555; Kurup, J sci industr Res, 1956, 15C, 153; Biol Abstr 1983, 76, 90469; Singh et. al., Indian For, 1958, 84, 571).

The flowers are reported to possess astringent, diuretic, depurative, aphrodisiac and tonic properties; they are used as an emmenagogue. They are also effective in leprosy, leucorrhoea and gout. An alcoholic concentrate of the petals showed anti-estrogenic activity at a dose of 3.2 mg/kg body-wt per day, in mice. A decoction of the flowers is given in diarrhoea and to puerperal women. The aqueous extract of the flowers show significant anti-implantation activity at a dose of 300 mg/kg body-wt in rats (Stewart, 60; Kirtikar & Basu, I, 787; Srivastava & Kumar, loc. cit.; Laumas & Uniyal, Indian J exp Biol, 1966, 4, 246; Prakash & Mathur, ibid, 1976, 14, 623; Bhatnagar et al, Indian J med Res, 1961, 49, 799; Khanna & Choudhury, ibid, 1968, 56, 1575).

The flowers contain butin, butein, butrin, isobutrin, palasitrin, coreopsin, isocoreopsin (butin-7-glucoside), sulphurein, monospermoside (butein-3-β-D-glucoside) and isomonospermoside. The major glycoside of the flower is butrin. The bright colour of the flowers is attributed to the presence of chalcones and aurones. The aqueous extract of the flowers, containing mainly the chalcone, isobutrin. (Dastur, Useful Plants, 54; Gupta, 180; Puri & Seshadri, J chem Soc, 1955, 1589; Gupta et. al., Phytochemistry, 1970, 9, 2231; Seshadri in Geissman, 9; Shimokoriyama in Geissman, 305; Oke et al, J Fd Sci, 1980, 45, 746).

Alcoholic extracts of the flowers exhibit significant anti-oestrogenic activity in mice. The ethyl acetate extract showed inhibition of uterus weight gain and vaginal epithelium cornification. The flowers and seeds are used against antifertility and anthelmintic properties. The dry powder of flowers is applied for healing wounds of camel and oxen. The poultice of flowers is applied to cure swollen and hanging testicles of children. An aqueous extract of flowers showed hepato-protective activity against $CCl_4$ induced liver injury in albino rats (Shah et. al., Indian J Pharm Sci, 1990, 52, 272; Vohra, Indian Drugs, 1989, 26, 526; Sharma et. al., Int J Pharmacogn, 1992, 30, 129; Nazimuddin et. al., Indian J Unani Med, 1991, 1,1). The petroleum and ethyl acetate extracts of the stem bark contain an anti-fungal compound (−)-3-hydroxy-9-methoxy ptero carpan also known as (−)-medicarpin, which was isolated as the acetate. Both (−)-medicaipin and its acetate were active against *Cladosporium cladosporioides* (Fres.) de Vries. The petroleum ether extract of the stem bark also yield lupenone, lupeol, sitosterol and the two isoflavons, 5-inethoxy-genistein and prunetin (Bandara et. al., J Nat Sci Coun, Sri Lanka, 1990, 18, 97).

*Butea parviflora*, is a gigantic, woody climber, 24 m in length and 90 cm or more in girth, common throughout India including the Andamans, ascending up to an altitude of 900 m. It is reported to be one of the most injurious climbers to trees on which it grows in the forest. Bark smooth, but rough on old stems, reddish brown; leaves 3-foliolate; leaflets sub-coriaceous, 10-23 cm×4 cm, variable in shape; flowers bright red to white or cream with a pink tinge, covered with feruginous tomentum, in large, terminal panicles; pods 7-10 cm×2.5 cm, 1-seeded.

*Butea superba* is a large, deciduous, woody climber, 90 cm in girth, found in the forests of Karnataka, Maharashtra, Gujarat, Andhra Pradesh, Orissa, Madhya Pradesh, Uttar Pradesh, Bihar and West Bengal. Leaflets 30-45 cm, sometimes up to 50 cm; flowers orange or orange scarlet, borne in great profusion along leafless branches, on 30 cm long racemes; pods 12.5-15 cm long. The bark is reported to be used in tonics, elixirs and in poultices. It exudes a reddish juice or gum.

EXAMPLE 1

Preparation of Extract from *Butea frondosa* by Percolation Method:

The dried material of flowers of *Butea frondosa* is pulverized to coarse powder and about 10 Kg of powdered material is placed in each of different flasks and extracted with chloroform, ethyl acetate, acetone, methanol, ethyl alcohol, water, mixture of methanol and water (1:1), acetone and water (1:1), acetone and water (7:3) and ethyl alcohol and water (1:1) at room temperature for 24 h to 48 h, then plant extracts are filtered and concentrated to dryness on rotatory evaporator or on steam bath at optimum temperature and under reduced pressure.

EXAMPLE 2

Preparation of Extract from *Butea frondosa* by Hot Soxhalation Method:

The coarse powdered material of flowers of *Butea frondosa* is subjected to hot soxhalation using solvents, chloroform, ethyl acetate, acetone, methanol, ethyl alcohol, water, mixture of methanol and water (1:1), acetone and water (1:1), acetone and water (7:3) and ethyl alcohol and water (1:1) at optimum temperature and recycled until extraction is complete, then plant extracts are filtered and concentrated to dryness on rotatory evaporator or on steam bath at optimum temperature.

All extracts, such as chloroform extract (PCPB-1), ethyl acetate extract (PCPB-2), acetone extract (PCPB-3), methanol extract (PCPB-4), ethyl alcohol extract (PCPB-5), water extract (PCPB-6), methanol and water (1:1) extract (PCPB-7), acetone and water (1:1) extract (PCPB-8), acetone and water (7:3) extract (PCPB-9) and ethyl alcohol and water (1:1) extract (PCPB-10), prepared from the flowers of *Butea frondosa* by using percolation method or hot soxhalation method were subjected to HPTLC (High Performance Thin Layer Chromatography) and HPLC (High performance Liquid chromatography) respectively for qualitative and quantitative estimation of marker compounds and active principles. It was found that the extracts PCPB-1 to PCPB-10 obtained from both methods were qualitatively and quantitatively similar to each other respectively.

EXAMPLE 3

Preparation of Extract from *Butea parviflora* by Percolation Method:

The dried material of stem bark of *Butea parviflora* is pulverized to coarse powder and about 10 Kg of powdered material is placed in each of different flasks and extracted with chloroform, ethyl acetate, acetone, methanol, ethyl alcohol, water, mixture of methanol and water (1:1), acetone and water (1:1), acetone and water (7:3) and ethyl alcohol and water (1:1) at room temperature for 24 h to 48 h, then plant extracts are filtered and concentrated to dryness on rotatory evaporator or on steam bath at optimum temperature and under reduced pressure.

EXAMPLE 4

Preparation of Extract from *Butea parviflora* by Hot Soxhalation Method:

The coarse powdered material of stem bark of *Butea parviflora* is subjected to hot soxhalation using solvents, chloroform, ethyl acetate, acetone, methanol, ethyl alcohol, water, mixture of methanol and water (1:1), acetone and water (1:1), acetone and water (7:3) and ethyl alcohol and water (1:1) at optimum temperature and recycled until extraction is completed, then plant extracts are filtered and concentrated to dryness on rotatory evaporator or on steam bath at optimum temperature.

All extracts, such as chloroform extract (PCPB-1P), ethyl acetate extract (PCPB-2P), acetone extract (PCPB-3P), methanol extract (PCPB-4P), ethyl alcohol extract (PCPB-5P), water extract (PCPB-6P), methanol and water (1:1) extract (PCPB-7P), acetone and water (1:1) extract (PCPB-5P), acetone and water (7:3) extract (PCPB-9P) and ethyl alcohol and water (1:1) extract (PCPB-10P), prepared from the flowers of *Butea frondosa* by using percolation method or hot soxhalation method were subjected to HPTLC (High Performance Thin Layer Chromatography) and HPLC (High performance Liquid chromatography) respectively for qualitative and quantitative estimation of marker compounds and active principles. It was found that the extracts PCPB-1P to PCPB-10P obtained from both methods were qualitatively and quantitatively similar to each other respectively.

EXAMPLE 5

Preparation of Extract from *Butea superba* by Percolation Method:

The dried material of exudates of stem and root of *Butea superba* is pulverized to coarse powder and about 10 Kg of powdered material is placed in each of different flasks and extracted with chloroform, ethyl acetate, acetone, methanol, ethyl alcohol, water, mixture of methanol and water (1:1), acetone and water (1:1), acetone and water (7:3) and ethyl alcohol and water (1:1) at room temperature for 24 h to 48 h, then plant extracts are filtered and concentrated to dryness on rotatory evaporator or on steam bath at optimum temperature and under reduced pressure.

EXAMPLE 6

Preparation of Extract from *Butea superba* by Hot Soxhalation Method:

The coarse powdered material of exudates of stem and root of *Butea superba* is subjected to hot soxhalation using solvents, chloroform, ethyl acetate, acetone, methanol, ethyl alcohol, water, mixture of methanol and water (1:1), acetone and water (1:1), acetone and water (7:3) and ethyl alcohol and water (1:1) at optimum temperature and recycled until extraction is completed, then plant extracts are filtered and concentrated to dryness on rotatory evaporator or on steam bath at optimum temperature.

All extracts, such as chloroform extract (PCPB-1S), ethyl acetate extract (PCPB-2S), acetone extract (PCPB-3S), methanol extract (PCPB-4S), ethyl alcohol extract (PCPB-5S), water extract (PCPB-6S), methanol and water (1:1) extract (PCPB-7S), acetone and water (1:1) extract (PCPB-8S), acetone and water (7:3) extract (PCPB-9S) and ethyl alcohol and water (1:1) extract (PCPB-10S), prepared from the flowers of Butea superba by using percolation method or hot soxhalation method were subjected to HPTLC (High Performance Thin Layer Chromatography) and HPLC (High performance Liquid chromatography) respectively for qualitative and quantitative estimation of marker compounds and active principles. It was found that the extracts PCPB-1S to PCPB-10S obtained from both methods were qualitatively and quantitatively similar to each other respectively.

EXAMPLE 7

Preliminary Screening of Extracts for Chemotherapy Induced Alopecia: Animals

Eight-day old rat pups of Sprague-Dawley strain of either sex, bred in Experimental Animal Facility of R&D Center, The Himalaya Drug Company, were used for the experiment. The animals were maintained at 22±3° C., 50-60% of humidity, 12 hours light and dark cycle.

Screening of Extracts in Chemotherapeutic Agent Induced Alopecia Model:

Three Groups of 8 rat pups are used. Group I served normal control and received saline at a dose of 10 ml/kg i.p. Group II & Group III animals received Cyclophosphamide (CP) at a dose of 50 mg/kg i.p. as a single dose. Test extracts PCPB-1 to PCPB-10, PCPB-1P to PCPB-10P and PCPB-1S to PCPB-10S were applied topically to Group III animals everyday from day one after Cyclophosphamide administration till the end of the study. On the $12^{th}$ day of post Cyclophosphamide injection, the animals were graded for alopecia as given below.

0—No detectable alopecia
1+—Mild alopecia
2+—Moderately severe alopecia with more than 50% hair loss
3+—Severe and total alopecia.

Results:

Hair Growth Effect of Different Extracts

Among different extracts screened for hair growth effects in chemotherapy induced alopecia model, PCPB-9, PCPB-9P and PCPB-9S have shown promising results and the details are given in Table-1 as follows.

The preliminary results have prompted us to carry out the study of the effects of combining extracts of the flowers of Butea frondosa, stem bark of Butea parviflora and stem and root exudates of Butea superba. Interestingly, acetone and water (7:3) extraction of all three plant material have showed excellent hair growth response.

EXAMPLE 8

Preparation of Aqueous Acetone Extract of Herbal Blend by Percolation Method:

The dried material of herbal blend comprising flowers of Butea frondosa (BF), stem bark of Butea parviflora (BP) and exudates or resins from stem and root of Butea superba (BS) are mixed in different combinations (Table 2) and pulverized to coarse powder. About 20 Kg of powdered material is placed in each of different flasks and extracted with acetone and water (7:3) at room temperature for 24 h to 48 h, then plant extracts are filtered and concentrated to dryness on rotatory evaporator or on steam bath at optimum temperature and under reduced pressure.

EXAMPLE 9

Preparation of Aqueous Acetone Extract of Herbal Blend by Hot Soxhalation Method:

The dried material of herbal blend comprising flowers of Butea frondosa (BF), stem bark of Butea parviflora (BP) and exudates or resins from stem and root of Butea superba (BS) are mixed in different combinations (Table 2) and pulverized to coarse powder. About 20 Kg of powdered material is placed in each of different flasks and extracted with acetone and water (7:3) at optimum temperature till extraction is completed and recycled again for the second time, then plant extracts are filtered and concentrated to dryness on rotatory evaporator or on steam bath at optimum temperature and under reduced pressure.

TABLE 2

| | Percentage of Plant materials in Herbal Blend | | |
|---|---|---|---|
| Extract Code No. | Butea frondosa | Butea parviflora | Butea superba |
| PCPB-20 | 20 | 40 | 40 |
| PCPB-30 | 25 | 25 | 50 |

TABLE 1

| Group | Animal | | | | | | | | Mean SEM |
|---|---|---|---|---|---|---|---|---|---|
| | 1 | 2 | 3 | 4 | 5 | 6 | 7 | 8 | |
| Normal Control | 0 | 0 | 0 | 0 | 0 | 0 | 0 | 0 | 0 |
| CP | +++ | +++ | +++ | ++ | +++ | +++ | +++ | +++ | 2.88 ± 0.13 |
| CP + PCPB-1 | +++ | ++ | +++ | +++ | ++ | +++ | +++ | +++ | 2.75 ± 0.16 |
| CP + PCPB-9 | + | 0 | + | ++ | + | + | 0 | ++ | 1.00 ± 0.27 |
| CP + PCPB-10 | +++ | +++ | +++ | +++ | +++ | ++ | +++ | +++ | 2.75 ± 0.16 |
| CP + PCPB-1P | +++ | +++ | +++ | +++ | +++ | ++ | +++ | +++ | 2.85 ± 0.13 |
| CP + PCPB-9P | + | + | ++ | + | + | ++ | + | + | 1.25 ± 0.16 |
| CP + PCPB-10P | +++ | ++ | +++ | +++ | ++ | +++ | +++ | +++ | 2.75 ± 0.16 |
| CP + PCPB-1S | +++ | ++ | +++ | +++ | ++ | +++ | +++ | +++ | 2.75 ± 0.16 |
| CP + PCPB-9S | + | ++ | 0 | + | ++ | + | + | + | 1.13 ± 0.23 |
| CP + PCPB-10S | +++ | +++ | +++ | +++ | +++ | ++ | ++ | +++ | 2.63 ± 0.18 |

TABLE 2-continued

| Extract Code No. | Percentage of Plant materials in Herbal Blend | | |
|---|---|---|---|
| | Butea frondosa | Butea parviflora | Butea superba |
| PCPB-40 | 40 | 40 | 20 |
| PCPB-50 | 50 | 25 | 25 |
| PCPB-60 | 60 | 30 | 10 |
| PCPB-70 | 70 | 20 | 10 |
| PCPB-80 | 80 | 10 | 10 |
| PCPB-90 | 80 | 0 | 20 |
| PCPB-100 | 80 | 20 | 0 |
| PCPB-110 | 70 | 10 | 20 |

Results:

The combined extracts PCPB-20 to PCPB-110 were subjected to screening as above in chemotherapeutic agent induced alopecia and results are summarized in Table 3 as below.

TABLE 3

| Group | Animal Number | | | | | | | | Mean SEM |
|---|---|---|---|---|---|---|---|---|---|
| | 1 | 2 | 3 | 4 | 5 | 6 | 7 | 8 | |
| Normal Control | 0 | 0 | 0 | 0 | 0 | 0 | 0 | 0 | 0 |
| CP | +++ | +++ | +++ | ++ | +++ | +++ | +++ | +++ | 2.88 ± 0.13 |
| CP + PCPB-20 | + | +++ | + | ++ | ++ | ++ | ++ | ++ | 1.88 ± 0.23 |
| CP + PCPB-30 | ++ | + | ++ | + | + | ++ | +++ | ++ | 1.75 ± 0.25 |
| CP + PCPB-40 | ++ | ++ | ++ | + | + | + | ++ | + | 1.50 ± 0.19 |
| CP + PCPB-50 | + | + | + | ++ | +++ | ++ | + | ++ | 1.75 ± 0.25 |
| CP + PCPB-60 | ++ | + | ++ | +++ | + | ++ | + | ++ | 1.75 ± 0.25 |
| CP + PCPB-70 | +++ | + | + | ++ | ++ | + | ++ | + | 1.63 ± 0.26 |
| CP + PCPB-80 | + | + | + | 0 | + | + | + | + | 0.88 ± 0.13 |
| CP + PCPB-90 | + | + | + | + | ++ | ++ | + | + | 1.25 ± 0.16 |
| CP + PCPB-100 | + | + | + | ++ | + | ++ | + | ++ | 1.38 ± 0.18 |
| CP + PCPB-110 | ++ | + | ++ | ++ | ++ | + | + | + | 1.50 ± 0.19 |

Chemical Composition of PCPB-80 Extract:

The most effective extract PCPB-80 was subjected to HPTLC, HPLC and chemical methods to identify the nature of marker compounds and for its quantitative estimation. High performance thin layer chromatography was performed over precoated silica gel plates (Merck) and run in different mobile phases for separation of compounds and identified different nature of compounds by spraying reagents like Dragon droff's reagent, ferric chloride reagent, vanillin-sulphuric acid reagent and anisaldehyde and sulphuric acid reagents etc. The quantitative estimation of each marker compounds is summarized in Table 4.

TABLE 4

| Sl. No. | Marker Compounds | Quantity (%) |
|---|---|---|
| 1 | Alkaloids | 0.17 |
| 2 | Cysteine | 4.50 |
| 3 | Aspartic acid | 0.1 |
| 4 | Procyanidins | 41.75 |
| 5 | Tannins | 28.80 |
| 6 | Flavonoids | 11.93 |
| 7 | Saponins | 0.32 |
| 8 | Glycosides | 17.61 |
| 9 | Reducing Sugars | 12.53 |
| 10 | Bitters | 3.19 |
| 11 | Fixed Oil | 0.18 |
| 12 | Anthraquinones | 0.32 |

Preparation of Hair Cream with PCPB-80:

TABLE 5

| Sl. No. | Ingredients | Percentage (%) |
|---|---|---|
| 1 | PCPB-80 Extract | 1.0 to 5.0 |
| 2 | Light liquid paraffin | 3.0 |
| 3 | Isopropyl myristate | 1.0 |
| 4 | Caprylic capric triglyceride | 0.5 |
| 5 | Cetyl alcohol | 1.0 |
| 6 | Cresmer 1000 | 0.8 |
| 7 | Glyceryl mono hydroxy stearate | 0.6 |
| 8 | Sorbitan stearate: | 0.6 |
| 9 | Polysorbate: 0.6 | 0.6 |
| 10 | BHT: 0.1 | 0.1 |
| 11 | Carbomer: 0.5 | 0.5 |
| 12 | Glycerin: 2.0 | 2.0 |
| 13 | EDTA: 0.05 | 0.05 |
| 14 | Triethanolamine: 0.4 | 0.4 |
| 15 | Preservative: qs. | 0.5 |
| 16 | Perfume: qs | qs |
| 17 | Water | Qs to 100% |

Preparation of Hair Gel with PCPB-80 Extract:

TABLE 6

| Sl. No. | Ingredients | Percentage (%) |
|---|---|---|
| 1 | PCPB-80 Extract | 1.0 to 2.5 |
| 2 | Carbomer | 0.5 |
| 3 | Triethanolamine | 0.2 |
| 4 | Sodium salt of methyl paraben | 0.2 |
| 5 | Sodium salt of propyl paraben | 0.1 |
| 6 | Glycerin | 5.0 |

TABLE 6-continued

| Sl. No. | Ingredients | Percentage (%) |
|---|---|---|
| 7 | Perfume | qs |
| 8 | Water | qs to 100% |

Clinical Trial of PCPB-80 Hair Cream in Human Beings:

A clinical trial with PCPB-80 hair cream was conducted at Seth Vadilal Sarabhai Gen. Hospital, Ahmedabad, India between January 2004 and March 2004 in 42 patients. Out of these, 35 patients were of diffuse hair loss and 7 patients were of alopaecia areata. The response to treatment was based on subjective and objective evaluation. Subjective evaluation criteria was number of hairs lost in 1 minute combing as follows:

| | |
|---|---|
| <50 | Excellent |
| 50-100 | Good |
| 100-150 | Fair |
| >150 | Poor |

Objective evaluation criteria was number of hairs in selected 1 cm scalp as follows:

| | |
|---|---|
| 2 fold increase in no. of hair follicles | Excellent |
| 1 fold increase in no. of hair follicles | Good |
| ½ fold increase in no. of hair follicles | Fair |
| No. increase | Poor |

Results:

All 35 patients of diffuse hair loss had excellent clinical results judged by the subjective and objective evaluation. 7 patients of alopaecia greata observed both subjectively and objectively 25% hair regrowth. None of the patients observed any untoward side effect.

Definitions

"Plant Extract" means and includes extracts of all plant parts of any of the herbs described herein.

What is claimed is:

1. A natural hair care composition for therapeutic treatment of hair loss comprising an effective amount of an aqueous acetone extract of the flowers of *Butea frondosa*, an aqueous acetone extract of the stem and root of *Butea superba* and an aqueous acetone extract of the stem bark of *Butea parviflora*, wherein the composition is in a cosmetically acceptable carrier.

2. The natural hair care composition according to claim 1, wherein said composition comprises an aqueous acetone extract of coarse powder of flowers of plant *Butea frondosa*.

3. The natural hair care composition according to claim 2, wherein aqueous acetone comprises a mixture of acetone and water in the ratio of 7:3.

4. The natural hair care composition according to claim 2, wherein the extract comprises Alkaloids, Amino acids, Procyanidins, Tannins, Flavonoids, Saponins, Glycosides, Reducing Sugars, Bitters, Fixed oil and Anthraquinones as active constituents.

5. The natural hair care composition according to claim 1, wherein said composition comprises an aqueous acetone extract of coarse powder of stem bark of plant *Butea parviflora*.

6. The natural hair care composition according to claim 1, wherein said composition comprises an aqueous acetone extract of coarse powder of exudates or resin from stem and root of plant *Butea superba*.

7. The composition according to claim 1, wherein said composition is for external application.

8. The composition according to claim 1, wherein said composition is in the form of cream or gel.

9. The natural hair care composition according to claim 1, wherein said cream composition comprises a therapeutically effective amount of the extract in an amount of 1% to 5% and cosmetically acceptable carrier comprising Light liquid paraffin 3.0%, Isopropyl myristate 1.0%, Caprylic capric triglyceride 0.5%, Cetyl alcohol 1.0%, cresmer 1000 0.8%, glyceryl mono hydroxy stearate 0.6%, sorbitan stearate 0.6%, polysorbate 0.6%, BHT 0.1%, Carbomer 0.5%, glycerin 2.0%, EDTA 0.05% and triethanolamine 0.4%.

10. The natural hair care composition according to claim 1, wherein the gel composition comprises the extract in an amount of 1% to 5% and cosmetically acceptable carrier comprising Carbomer 0.5%, triethanolamine 0.2%, sodium salt of methyl paraben 0.2%, propyl paraben 0.1% and glycerin 5%.

11. The natural hair care composition according to claim 1, wherein the composition comprises a potency equivalent of the extract ranging from 1% to 5%.

12. The natural hair care composition according to claim 1, wherein the combination comprises 20 to 80 weight percent *Butea frondosa*; 10 to 40 weight percent *Butea superba*; and 10 to 50 weight percent *Butea parviflora*.

13. The natural hair care composition according to claim 1, wherein the combination comprises plants *Butea frondosa*, *Butea superba* and *Butea parviflora* in the ratio of 80:10:10, respectively.

* * * * *